United States Patent [19]

Horii et al.

[11] Patent Number: 4,486,602

[45] Date of Patent: Dec. 4, 1984

[54] VALIENAMINE DERIVATIVES, THEIR PRODUCTION AND USE

[75] Inventors: Satoshi Horii, Sakai; Yukihiko Kameda, Kanazawa; Hiroshi Fukase, Osaka, all of Japan

[73] Assignee: Takeda Chemical Industries, Ltd., Osaka, Japan

[21] Appl. No.: 306,774

[22] Filed: Sep. 29, 1981

[30] Foreign Application Priority Data

Oct. 6, 1980 [JP] Japan .................. 55-140172

[51] Int. Cl.$^3$ .................. C07C 91/18; C12N 9/96
[52] U.S. Cl. .................. 564/360; 564/316; 564/353; 564/355; 564/363; 564/364; 564/374; 564/376; 564/381; 564/382; 564/383; 564/384; 564/386; 564/389; 564/391; 564/392; 564/462; 435/188
[58] Field of Search .......... 564/462, 360, 363, 374, 564/381, 389

[56] References Cited

U.S. PATENT DOCUMENTS

| | | | |
|---|---|---|---|
| 3,240,785 | 3/1966 | Martin | 564/462 X |
| 3,609,156 | 9/1971 | Hideaki et al. | 564/462 X |
| 3,652,769 | 5/1972 | Saari | 564/462 X |
| 4,062,950 | 12/1979 | Frommer et al. | 424/181 |

OTHER PUBLICATIONS

Offenlegungsschrift (Germany), Offenlegungstag. 16. 8. 79 Section Class Subclass/C12D.

*Primary Examiner*—Robert V. Hines
*Attorney, Agent, or Firm*—Wegner & Bretschneider

[57] ABSTRACT

A compound of the formula:

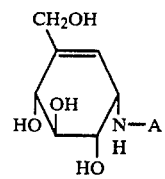

wherein A is a chain hydrocarbon group having 1 to 10 carbon atoms optionally substituted by hydroxyl, phenoxy, thienyl, furyl, pyridyl, cyclohexyl or an optionally substituted phenyl group; or a cyclic hydrocarbon group having 3 to 7 carbon atoms optionally substituted by hydroxyl, and their production and use.

These compounds exhibit excellent inhibitory activity against glucoside hydrolase, thus are useful for hyperglycemic symptoms and various disorders caused by hyperglycemia.

5 Claims, No Drawings

VALIENAMINE DERIVATIVES, THEIR PRODUCTION AND USE

The present invention relates to N-substituted derivatives of valienamine having the inhibitory activity against glucoside hydrolase, to processes for producing the same, and to α-glucosidase inhibitors containing the above-mentioned derivatives.

The present inventors previously discovered and isolated, for the first time, the compound of the formula:

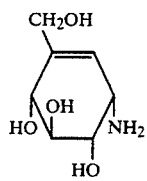

[II]

as a constituent of validamycin, an antibiotic. The compound was named "valienamine" and reported (Kameda and Horii: Journal of the Chemical Society; Chemical Communications, 1972, 746 to 747). Furthermore, the extensive research subsequently carried out has led us to the finding that valienamine possesses a highly valuable action of suppressing the function of α-glucoside hydrolase. The finding was further followed by continued studies on various novel derivatives of valienamine, and as a result, it was found that a group of N-substituted derivatives of valienamine exhibits stronger activity then valienamine itself, which has culminated in the present invention. Thus, the present invention relates to:

1. A compound of the formula:

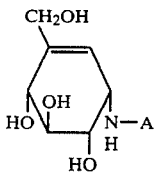

[I]

wherein A is a chain hydrocarbon group having 1 to 10 carbon atoms optionally substituted by hydroxyl, phenoxy, thienyl, furyl, pyridyl, cyclohexyl or an optionally substituted phenyl group; or a cyclic hydrocarbon group having 3 to 7 carbon atoms optionally substituted by hydroxyl;

2. A process for producing a compound [I] which comprises reacting a chain aldehyde or ketone having 1 to 10 carbon atoms optionally substituted by hydroxyl, phenoxy, thienyl, furyl, pyridyl, cyclohexyl or an optionally substituted phenyl group; or a cyclic ketone having 3 to 7 carbon atoms optionally substituted by hydroxyl with valienamine, and subjecting the resultant to reduction;

3. A process for producing a compound [I] which comprises reacting a chain hydrocarbon halide having 1 to 10 carbon atoms optionally substituted by hydroxyl, phenoxy, thienyl, furyl, pyridyl, cyclohexyl or an optionally substituted phenyl group; or a cyclic hydrocarbon halide having 3 to 7 carbon atoms optionally substituted by hydroxyl, with valienamine;

4. A process for producing a compound of the formula:

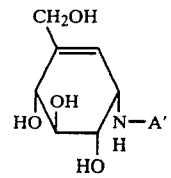

[I']

wherein A' is a chain hydrocarbon group having 2 to 10 carbon atoms optionally substituted by hydroxyl, phenoxy, thienyl, furyl, pyridyl, cyclohexyl or an optionally substituted phenyl group; or a cyclic hydrocarbon group having 3 to 7 carbon atoms optionally substituted by hydroxyl which comprises reacting a compound of the formula:

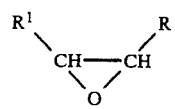

[III]

wherein $R^1$ is hydrogen, and R is hydrogen, hydroxyl, phenoxy, thienyl, furyl, pyridyl, cyclohexyl or an optionally substituted phenyl group; or a chain hydrocarbon group having 1 to 8 carbon atoms optionally substituted by hydroxyl, phenoxy, thienyl, furyl, pyridyl, cyclohexyl or an optionally substituted phenyl group, or $R^1$ and R may form together with the adjacent methine group a cyclic hydrocarbon of 3 to 7 carbon atoms optionally substituted by hydroxyl, with valienamine; and 5. α-Glucosidase inhibitor containing a compound [I].

Referring to the compounds [I], the chain hydrocarbon group of 1 to 10 carbon atoms represented by A includes straight-chain saturated, aliphatic hydrocarbon groups such as methyl, ethyl, propyl, butyl, pentyl, hexyl, heptyl, octyl, nonyl and decyl; branched saturated, aliphatic hydrocarbon groups, such as isopropyl, isobutyl, sec-butyl, tert-butyl, isopentyl, neopentyl, tert-pentyl, 1-methylbutyl, 2-methylbutyl, isohexyl, 1-methylpentyl, 2-methylpentyl, 3-methylpentyl, 4-methylpentyl, methylhexyl exemplified by 5-methylhexyl, etc., methylheptyl exemplified by 1-methylheptyl, etc., methyloctyl, methylnonyl, 1-ethylpropyl, ethylbutyl, ethylpentyl, ethylhexyl, ethylheptyl, ethyloctyl, 1-methylisobutyl, 1-methylisopentyl, dimethylbutyl exemplified by 1,1-dimethylbutyl, etc., dimethylpentyl exemplified by 1,1-dimethylpentyl, 1,4-dimethylpentyl, etc., dimethylhexyl, dimethylheptyl, dimethyloctyl, ethylmethylpropyl exemplified by 1-ethyl-1-methylpropyl, etc., ethylmethylbutyl exemplified by 1-ethyl-2-methylbutyl, 1-ethyl-3-methylbutyl, etc., and propylbutyl exemplified by 1-isopropylbutyl, etc.; and straight-chain and branched unsaturated aliphatic hydrocarbon groups such as propenyl exemplified by vinyl, allyl, etc., butenyl exemplified by 3-butenyl, etc., pentenyl exemplified by 4-pentenyl, etc., hexenyl, heptenyl, octenyl, nonenyl, decenyl, butadienyl, pentadienyl, hexadienyl, heptadienyl, octadienyl, nonadienyl, decadienyl, hexatrienyl, heptatrienyl, octatrienyl, nonatrienyl, decatrienyl, octatetraenyl, nonatetraenyl, decatetraenyl, decapentaethyl, isopropenyl, methylpropenyl exemplified by 2-methylallyl, etc., dimethylpropenyl exemplified by 1,1-dimethylallyl, etc., methylbutenyl, exemplified by 3-methyl-2-butenyl, 3-methyl-3-butenyl, etc., and dimethyldienyl unsaturated hydrocarbon groups exemplified by 3,7-dimethyl-2,6-octadienyl, etc. As preferable ones among them, there may be mentioned chain hydrocarbons of 1 to 6 carbon atoms. Further, these hydrocarbon groups may be substituted by one or more of hydroxyl, cyclohexyl, phenoxy, thienyl, furyl, pyridyl or a phenyl group which may be substituted with hydroxy, lower alkoxy such as methoxy and ethoxy, carboxyl, halogen atom such as chlorine, bromine and iodine, phenyl or lower alkyl such as methyl, ethyl, propyl, isopropyl, butyl, sec-butyl and tert-butyl, preferably the above-mentioned substituents are hydroxyl or phenyl groups which may be substituted by hydroxy, lower alkoxy, lower alkyl or halogen. The cyclic hydrocarbon group of 3 to 7 carbon atoms represented by A includes cyclic saturated hydrocarbon groups such as cyclopropyl, cyclobutyl, cyclopentyl, cyclohexyl and cycloheptyl; cyclic unsaturated hydrocarbon groups such as cyclopropenyl, cyclobutenyl, cyclopentenyl, cyclohexenyl and cycloheptenyl. As preferable ones among them, there may be mentioned cyclic hydrocarbons of 5 to 6 carbon atoms. These cyclic hydrocarbon groups may be optionally substituted by one to six hydroxyl groups.

Furthermore, specific examples of the N-substituted valienamine derivatives represented by the formula [I] include:
N-benzylvalienamine;
N-phenethylvalienamine;
N-(3-phenylpropyl)valienamine;
N-(4-phenylbutyl)valienamine;
N-(5-phenylpentyl)valienamine;
N-(6-phenylhexyl)valienamine;
N-(3-phenylallyl)valienamine;
N-furfurylvalienamine;
N-thenylvalienamine;
N-(3-pyridylmethyl)valienamine;
N-(4-methylbenzyl)valienamine;
N-(4-methoxybenzyl)valienamine;
N-(3-phenoxypropyl)valienamine;
N-(2-phenylpropyl)valienamine;
N-n-butylvalienamine;
N-(4-bromobenzyl)valienamine;
N-(4-carboxybenzyl)valienamine;
N-($\beta$-hydroxyphenethyl)valienamine;
N-($\beta$-hydroxy-2-methoxyphenethyl)valienamine;
N-($\beta$-hydroxy-2-chlorophenethyl)valienamine;
N-($\alpha$-methylbenzyl)valienamine;
N-($\alpha$-methylphenethyl)valienamine;
N-(4-hydroxybenzyl)valienamine;
N-(3,5-di-tert-butyl-4-hydroxybenzyl)valienamine;
N-(2-diphenylethyl)valienamine;
N-(cyclohexylmethyl)valienamine;
N-geranylvalienamine;
N-(1,3-dihydroxy-2-propyl)valienamine;
N-(D-gluco-2,3,4,5,6-pentahydroxyhexyl)valienamine;
N-(D-manno-2,3,4,5,6-pentahydroxyhexyl)valienamine;
N-(D-galacto-2,3,4,5,6-pentahydroxyhexyl)valienamine;
N-(D-arabo-2,3,4,5-tetrahydroxypentyl)valienamine;
N-(D-ribo-2,3,4,5-tetrahydroxypentyl)valienamine;
N-(D-xylo-2,3,4,5-tetrahydroxypentyl)valienamine;
N-(D-arabo-2,3,4,5-tetrahydroxy-1-hydroxymethylpentyl)-valienamine;
N-(L-xylo-2,3,4,5-tetrahydroxy-1-hydroxymethylpentyl)-valienamine;
N-(2-hydroxycyclohexyl)valienamine;
N-(2-hydroxycyclopentyl)valienamine.

The $\alpha$-glucosidase inhibitor of the present invention, because of its ability to suppress the metabolism of carbohydrates in man and other animals, exhibits the blood-sugar elevation suppressing function, and is a compound useful for hyperglycemic symptoms and various disorders caused by hyperglycemia such as obesity, adiposity, hyperlipemia (arteriosclerosis), diabetes, and prediabetes as well as diseases attributable to sugar metabolism by microorganisms in oral cavity such as prophylaxis of dental caries. Foods prepared by adding compounds [I] are useful as a therapeutic diet for patients affected with metabolic abnormality and as a prophylactic diet for healthy persons, as well. In addition, the derivatives are of use as an additive for livestock feed which helps to obtain low-fat, high-quality animal flesh for food. Therefore, the $\alpha$-glucosidase inhibitors of the present invention are of value as drugs, food additives and livestock feed additives. The $\alpha$-glucosidase inhibitors of the present invention are administered orally or parenterally, preferably orally.

The above-mentioned compounds [I] are stable crystals or powders and almost free from toxicity ($LD_{50}$ in rats, not lower than 1000 mg), and can be utilized as a free base or hydrate and also as any non-toxic acid addition salts formed with pharmacologically allowable acids by conventional methods. As examples of such acids, use is made of inorganic acids such as hydrochloric acid, hydrobromic acid, sulfuric acid, phosphoric acid and nitric acid, and orgnaic acids such as acetic acid, malic acid, citric acid, ascorbic acid, mandelic acid and methanesulfonic acid. Such derivative's of valienamine are used solely or as mixtures with non-toxic carriers, and may be utilized with liquid or solid foods such as coffee, beverages, fruit juice, beer, milk, jam and bean jam seasoning agents, or the principal and subsidiary foods, etc. They can be used directly or in the form of a food additives, or can be administered before or after meals. Further, they can also find application as additives for livestock feed which serve to obtain low-fat, high-quality animal flesh for food.

The inhibitors of the present invention can be diluted with non-toxic carriers, for example, such liquid carries as water, ethanol, ethylene glycol and polyethylene glycol, and such solid carriers as starch, cellulose and polyamide powders, and prepared into ampoules, granules, tablets, pills, capsules, syrups, etc. by conventional methods to utilize in the above-mentioned, various application fields. In addition, they can also be used in combination with sweetening, preservatives, dispersing agents and coloring agents.

Specifically, preparations containing for example 20 to 300 mg of the valienamine derivative, when given after each meal, can suppress elevation in blood concentrations of glucose brought about by ingestion. Furthermore, the compounds [I] may be added to various foods at ratios in the range of 0.01 to 1% of a carbohydrate content in the food.

In the case of blending in livestock feed, it is desirable to add at ratios of 0.001 to 1% of a carbohydrate content in feed.

The compounds [I] of the present invention are all the novel compounds that have not been described in the literature, and can be synthesized for example by the following method: that is to say, they can be synthesized by subjecting to a reduction reaction a Schiff's base obtained by reacting with valienamine in an appropriate solvent a chain aldehyde or ketone of 1 to 10 carbon atoms optionally substituted by hydroxyl, phenoxy, thienyl, furyl, pyridyl, cyclohexyl or an optionally substituted phenyl group. The condensation reaction of an amino group in valienamine with aldehyde or ketone and the subsequent reduction reaction may be consecutively conducted in the same reaction vessel, or the reactions may be carried out separately in two stages. As the reaction solvent, use can be made of water, alcohols such as methanol, propanol and butanol, dimethylsulfoxide, dimethylformamide, N-methylacetamide, glymes such as methyl cellosolve, dimethyl cellosolve and diethylene glycol dimethyl ether, polar solvents such as dioxanes, tetrahydrofuran and acetonitrile, or their mixed solvents, or mixtures of these polar solvents with non-polar solvents such as chloroform and dichloromethane.

The reaction temperature in the Schiff's base formation reaction is not particularly limited, and the reaction is carried out by heating at temperature in the range of room temperature to 100° C. The reaction time varies depending upon the reaction temperature and the type of aldehydes or ketones used, but the desired objective can be achieved normally by allowing the reaction to proceed for a period in the range of several minutes to 24 hours.

The reduction reaction of a formed Schiff's base is required to be conducted under such conditions as may not allow hydrogenation of a double bond in the valienamine moiety. For the purpose of this, use is advantageously made of a variety of reducing agents based on metal hydride complexes, such as alkali-metal borohydrides, e.g., sodium borohydride, potassium borohydride, lithium borohydride and sodium trimethoxy borohydride, alkali-metal cyanoborohydrides, e.g., sodium cyanoborohydride, alkalimetal aluminium hydrides, e.g., lithium aluminium hydride, and dialkylamine boranes, e.g. dimethylamine borane. In cases in which alkali-metal cyanoborohyrides such as sodium cyanoborohydride are used, further, it is desirable to conduct the reaction under acid conditions, for example, in the presence of hydrochloric acid, acetic acid, etc.

The reaction temperature is not particularly limited, and the reaction is conducted normally at room temperature or, as the case may be, by heating at temperature up to about 100° C.; the reaction temperature varies depending upon the type of Schiff's bases and the kind of reducing agents. The reaction time also varies according to the reaction temperature and the kinds of Schiff's bases to be reduced and reducing agents, and the desired object can be attained normally by allowing the reaction to proceed for a period in the range of several minutes to 24 hours.

The compound [I] can be synthesized by reacting with valienamine in an appropriate solvent a chain hydrocarbon halide of 1 to 10 carbon atoms optionally substituted by hydroxyl, phenoxy, thienyl, furyl, pyridyl, cyclohexyl or an optionally substituted phenyl group.

As the appropriate reaction solvent, use is made of water, lower alkanols such as methanol, ethanol, propanol and butanol, ketones such as acetone, methyl ethyl ketone and methyl isobutyl ketone, dimethylsulfoxide, dimethylformamide, N-methylacetamide, glymes such as methyl cellosolve, ethylene glycol dimethyl ether and diethylene glycol dimethyl ether, polar solvents such as dioxane, tetrahydrofuran and acetonitrile, or their mixed solvents, or mixed solvents of these with non-polar solvents such as benzene, hexane, chloroform, dichloromethane and ethyl acetate, and others. In cases in which such mixed solvent do not present the homogeneous phase, the reaction may be conducted in the presence of a phase-transfer catalyst such as tert-ammonium salt (e.g. tetrabutyl ammonium bromide), crown ether (e.g. dibenzo-18-crown-6) and phosphonium salt (e.g. hexadecyltri-n-butylphosphonium bromide).

As a proton acceptor, use can be made of inorganic and organic bases such as alkali-metal bicarbonates, alkali-metal carbonates, alkali-metal hydroxides, trimethylamine, triethylamine, tributylamine, N-methylmorpholine, N-methylpiperidine, N,N-dimethylaniline, pyridine, picoline and lutidine.

The reaction temperature is not particularly limited, and the reaction is conducted normally at room temperature or by heating at temperature up to about 100° C. The reaction time varies depending upon the reaction temperature, and the desired objective can be achieved normally by allowing the reaction to proceed for a period in the range of several minutes to 24 hours. The compound [I'] can be synthesized by the reaction of valienamine with a compound [III] in an appropriate solvent.

As the appropriate reaction solvent, use is made of water, lower alkanols such as methanol, ethanol, propanol and butanol, ketones such as acetone, methyl ethyl ketone and methyl isobutyl ketone, dimethylsulfoxide, dimethylformamide, N-methylacetamide, glymes such as methyl cellosolve, ethylene glycol dimethyl ether and diethylene glycol dimethyl ether, polar solvents such as dioxane, tetrahydrofuran and acetonitrile, or their mixed solvents, or mixed solvents of these with non-polar solvents such as benzene, hexane, chloroform, dichloromethane and ethyl acetate, and others. In cases in which such mixed solvents do not present the homogeneous phase, the reaction may be conducted in the presence of a phase-transfer catalyst such as crown ether, phosphorium salt and tert-ammonium salt.

The reaction temperature is not particularly limited, and the reaction is conducted normally at room temperature or by heating at temperature up to about 100° C. The reaction time varies depending upon the reaction temperature, and the desired object can be achieved normally by allowing the reaction to proceed for a period in the range of several minutes to 24 hours.

The compound [I] can also be synthesized by the reaction of valienamine with β-halohydrin or by first synthesizing an N-acylvalienamine derivative, followed by the reduction to methylene of carbonyl in its amide linkage by use of alkali-metal aluminium hydrides such as lithium aluminium hydride.

Below described are the reference examples and examples to illustrate in detail the contents of the present invention.

REFERENCE EXAMPLE

The α-glucosidase inhibitory activity

Procedure

The inhibitory activity of the compounds of this invention against α-glucosidase (yeast, type I, produced by Sigma Chemicals, U.S.A.), when p-nitrophenyl-α-D-glucopyranoside is used as a substrate, is determined by adding 0.5 ml of a solution of an inhibitor of this invention in 0.02M phosphate buffer (pH 6.8) and 0.25 ml of 0.01M p-nitrophenyl-α-D-glucopyranoside in the same buffer to 0.25 ml of a solution of α-glucosidase in the same buffer (0.005 mg/ml), allowing the reaction to proceed at 37° C. for 15 minutes, then adding 3 ml of 0.1M aqueous sodium carbonate solution to terminate the reaction, and measuring the absorbance of the reaction solution at 400 nm. The 50% inhibition concentration of the inhibitor is calculated from the inhibition rates (%) which are determined with inhibitory substance samples of three to five different concentrations.

When 0.05M maltose is used as a substrate, the inhibitory activity against maltase prepared from porcine intestinal mucosa is determined by measuring the amount of released D-glucose by use of glucose oxidase [Glucose B-Test Wako (a reagent for clinical diagnostic use for determining glucose, produced by Wako Pure Chemical Co. Japan)] to calculate the 50% inhibition concentration. The molar concentration required for 50% inhibition ($IC_{50}$) of the α-glucosidase inhibitors represented by the formula [I], to inhibit activity of α-glucosidase (yeast), is shown in Table 1 and that to inhibit activity of maltase (porcine intestinal mucosa) is in Table 2.

TABLE 1

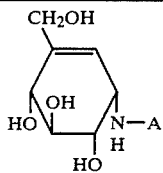

[I]

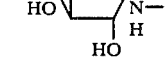

TABLE 1-continued

Compound [I]:

Structure: cyclohexene ring with CH2OH, OH groups and N–A (H on N), HO substituents.

| A | $[\alpha]_D^{25}$ | $IC_{50}$ (M) |
|---|---|---|
| $-CH(CH_2OH)_2$ | +111.0° (c = 1, H$_2$O) | $0.66 \times 10^{-4}$ |
| $-CH_2-C(OH)(H)-C(H)(OH)-C(OH)(H)-C(H)(OH)-CH_2OH$ | +75.5° (c = 1, H$_2$O) | $0.11 \times 10^{-3}$ |
| $-CH_2-C(OH)(H)-C(H)(OH)-C(H)(OH)-C(OH)(H)-CH_2OH$ | +88.9° (c = 1, H$_2$O) | $0.16 \times 10^{-3}$ |
| $-CH(CH_2OH)-C(H)(OH)-C(OH)(H)-C(OH)(H)-CH_2OH$ | +88.2° (c = 1, H$_2$O) | $0.11 \times 10^{-3}$ |
| $-CH_2-C(H)(OH)-C(H)(OH)-C(OH)(H)-CH_2OH$ (H,H,OH,OH,OH,H config) | +93.9° (c = 1, H$_2$O) | $0.10 \times 10^{-3}$ |
| $-CH_2-C(H)(OH)-C(OH)(H)-C(OH)(H)-CH_2OH$ | +97.2° (c = 1, H$_2$O) | $0.12 \times 10^{-3}$ |
| $-CH_2-C(OH)(H)-C(OH)(H)-C(OH)(H)-CH_2OH$ | +30.3° (c = 1, H$_2$O) | $0.90 \times 10^{-4}$ |
| $-CH_2-C(OH)(H)-C(H)(OH)-C(OH)(H)-CH_2OH$ | +153.6° (c = 1, H$_2$O) | $0.11 \times 10^{-3}$ |
| $-CH(CH_2OH)-C(H)(OH)-C(OH)(H)-C(H)(OH)-CH_2OH$ | +103.5° (c = 1, H$_2$O) | $0.13 \times 10^{-3}$ |

TABLE 2

| A | $IC_{50}$ (M) |
|---|---|
| $-CH_2CH_2-C_6H_5$ | $0.11 \times 10^{-4}$ |
| $-(CH_2)_3-C_6H_5$ | $0.20 \times 10^{-4}$ |
| $-(CH_2)_4-C_6H_5$ | $0.80 \times 10^{-4}$ |
| $-CH_2-CH(OH)-C_6H_5$ | $0.32 \times 10^{-5}$ |
| $-CH_2-C_6H_4-Br$ | $0.75 \times 10^{-4}$ |
| $-CH_2-C_6H_4-OH$ | $0.19 \times 10^{-4}$ |
| $-CH_2CH(OH)-CH_2-O-C_6H_5$ · HCl | $0.24 \times 10^{-4}$ |
| $-CH(CH_2OH)-C_6H_5$ | $0.14 \times 10^{-4}$ |
| $-CH(CH_3)-CH_2-C_6H_5$ | $0.24 \times 10^{-5}$ |
| $-CH_2-CH(OH)-C_6H_4(OCH_3)$ | $0.31 \times 10^{-5}$ |
| $-CH_2-CH=C(CH_3)-CH_2-CH_2-CH=C(CH_3)_2$ (geranyl-type) | $0.52 \times 10^{-5}$ |
| $-CH(CH_2OH)_2$ | $0.14 \times 10^{-4}$ |
| $-CH(CH_2OH)-C(H)(OH)-C(OH)(H)-C(H)(OH)-CH_2OH$ | $0.14 \times 10^{-4}$ |
| $-CH(CH_2OH)(OH)-CH(C_6H_5)$ · HCl | $0.96 \times 10^{-5}$ |
| $-CH_2-C_6H_3(OH)_2$ | $0.81 \times 10^{-5}$ |

EXAMPLE 1

N-benzylvalienamine

In 90 ml of a methanol-dioxane (2:1) mixture is dissolved 4.0 g of valienamine, and 2.6 g of sodium hydrogen carbonate and 2.6 ml of benzyl bromide are added to the solution, followed by stirring at room temperature for 18 hours. The reaction mixture is filtered, and the filtrate is concentrated under reduced pressure. To the concentrate are added water and ethyl acetate, and the mixture is stirred, followed by separating the reaction mixture into two layers. N,N-dibenzylvalienamine as the by-product is in the ethyl acetate layer. The water layer is subjected to extraction with n-butanol, and the n-butanol extract, after adding water thereto, is subjected to azeotropic distillation under reduced pressure to remove the n-butanol. Then, N-benzylvalienamine separates out as crystals from the aqueous solution, Yield of 1.8 g.

mp: 151°–155° C. (decomp.)

Elemental analysis, for $C_{14}H_{19}NO_4$

Calcd.(%): C, 63.38; H, 7.22; N, 5.28 Found (%): C, 63.43; H, 7.21; N, 4.93

EXAMPLE 2

N-thenylvalienamine

In 20 ml of methanol is dissolved 2.0 g of valienamine. To the solution is added 2 ml of 2-thiophenecarbaldehyde. The mixture is stirred at room temperature for 1 hour. The reaction solution is concentrated under reduced pressure. To the concentrate is added ethyl ether. The resulting precipitates are collected by filtration and dried. 3.1 g of the resulting Schiff's base is dissolved in 30 ml of methanol, and 425 mg of sodium borohydride is added little by little to the solution under ice-cooling, followed by further stirring for 1 hour. To the reaction solution are added acetone and water. The mixture is concentrated under reduced pressure, and the resultant aqueous solution is chromatographed on a column (250 ml) of Diaion HP-20AG (manufactured by Mitsubishi Chemical Ind., Ltd. Japan). The column is washed with water (500 ml), and the elution is carried out with a gradient of water (1 l)—80% aqueous methanol (1 l). The eluate (fraction No.68–85, one fraction weighs 18 g) is concentrated under reduced pressure to give crystals of N-thenylvalienamine. Yield of 1.7 g.

Elemental analysis, for $C_{12}H_{17}NO_4S$

Calcd.(%): C, 53.12; H, 6.32; N, 5.16; S, 11.82 Found (%): C, 53.39; H, 6.46; N, 5.27; S, 11.91

EXAMPLE 3

N-furfurylvalienamine

In 20 ml of methanol is dissolved 2 g of valienamine. To the solution is added 2 ml of 2-furaldehyde, and the mixture is stirred at room temperature for 2 hours. The reaction solution is concentrated under reduced pressure. To the concentrate is added ethyl ether and, the resultant precipitate is collected by filtration. 2.45 g of the Schiff's base thus obtained is dissolved in 30 ml of methanol. To the solution is added 340 mg of sodium borohydride under ice-cooling. The mixture is stirred at the same temperature for 1 hour. To the reaction mixture are added n-butanol, acetone and water. The mixture is then concentrated under reduced pressure to distill off the organic solvent. The resultant aqueous solution is chromatographed on a column (250 ml) of Diaion HP-20AG. The column is washed with water, and the elution is carried out with a gradient of water (1 l)—50% aqueous methanol (1 l). The eluate (fraction No. 55–78, one fraction weighs 18 g) is concentrated under reduced pressure and lyophilized to give N-furfurylvalienamine. Yield of 1.9 g.

Elemental analysis, for $C_{12}H_{17}NO_5$

Calcd.(%): C, 56.46; H, 6.71; N, 5.49 Found (%): C, 56.17; H, 6.85; N, 5.76

EXAMPLE 4

N-(3-pyridylmethyl)valienamine

In 20 ml of methanol is dissolved 2 g of valienamine. To the solution is added 1.2 ml of nicotinaldehyde. The solution is stirred at room temperature for 1 hour. To the reaction mixture is added ethyl ether, and the resultant precipitate is recovered by filtration. 2.2 g of the Schiff's base thus obtained is suspended in 30 ml of methanol. To the suspension is added 300 mg of sodium borohydride under ice-cooling, and the mixture is stirred at the same temperature for 1 hour. Then, 100 mg of sodium borohydride is further added to the mixture, which is stirred at room temperature for 1 hour. Aqueous acetone and n-butanol are added to the reaction mixture, and the mixture is concentrated under reduced pressure. The residue is chromatographed on a column (250 ml) of Diaion HP-20AG, and the elution is carried out with a gradient of water (1 l) 80% aqueous methanol (1 l). The eluate (fraction No. 39–55, one fraction weighs 18 g) is concentrated under reduced pressure and then lyophilized to give N-(3-pyridylmethyl)valienamine.

Elemental analysis, for $C_{13}H_{18}N_2O_4$

Calcd.(%): C, 58.63; H, 6.81; N, 10.52 Found (%): C, 58.17; H, 6.96; N, 10.48

EXAMPLE 5

N-(cyclohexylmethyl)valienamine

In 80 ml of dimethylformamide is dissolved 3 g of valienamine. To the solution are added 5.04 g of sodium hydrogen carbonate and 4 ml of cyclohexylmethyl bromide. The mixture is stirred for 18 hours under heating at 60° to 65° C. The reaction solution is concentrated under reduced pressure. To the concentrate is added water, and the pH is adjusted to 2, followed by washing with toluene. The water layer is adjusted to pH 10, and then extracted with three portions of n-butanol. The n-butanol extracts are combined, washed once with water and concentrated under reduced pressure. Water is added to the concentrate to give crystals of N-(cyclohexylmethyl)valienamine. Yield of 0.7 g.

Elemental analysis, for $C_{14}H_{25}O_4N$

Calcd.(%): C, 61.96; H, 9.29; N, 5.16

Found (%): C, 61.89; H, 9.05; N, 5.19

EXAMPLE 6

N-(4-hydroxybenzoyl)valienamine

In 20 ml of methanol is dissolved 2.0 g of valienamine. To the solution is added 2.4 g of p-hydroxybenzaldehyde, followed by stirring at room temperature for 1 hour. To the reaction mixture is added ethyl ether, and the resultant crystals are collected by filtration and dried. 2.7 g of the Schiff's base thus obtained is suspended in 25 ml of methanol. To the suspension is added 380 mg of sodium borohydride under ice-cooling, followed by stirring for 2 hours. To the reaction mixture are added water and acetone. The mixture is concentrated under reduced pressure to distill off the organic solvent. The concentrated solution is chromatographed on a column (250 ml) of Amberlite CG-50 ($NH_4^+$ type) (manufactured by Rohm & Haas Co., U.S.A.), and the elution is carried out with water. The eluate is concentrated under reduced pressure, and the concentrate is further chromatographed on a column (250 ml) of Diaion HP-20AG, followed by conducting the elution with a gradiant of water (1 l)-80% aqueous methanol (1 l). The eluate (fraction No. 37-62, one fraction weighs 18 g) is concentrated under reduced pressure and lyophilized to give 1.75 g of N-(4-hydroxybenzyl)valienamine.

EXAMPLE 7

N-(4-methoxybenzyl)valienamine

In 20 ml of methanol is dissolved 2.0 g of valienamine. To the solution is added 2.5 g of p-anisaldehyde, followed by stirring at room temperature for 2 hours. Ethyl ether is added to the reaction solution, and the resultant precipitate is collected by filtration and dried. The resultant Schiff's base is dissolved in 30 ml of methanol. To the solution is added 400 mg of sodium borohydride under ice-cooling, followed by stirring for 1 hour. Water and acetone are added to the reaction solution, to which n-butanol is added. The mixture is subjected to concentration under reduced pressure azeotropically to remove the organic solvent. The resultant aqueous solution is extracted with n-butanol, and the n-butanol extract, together with water, is subjected to concentration under reduced pressure azeotropically to give crystals of N-(4-methoxybenzyl)valienamine. Yield of 1.5 g.

Elemental analysis, for $C_{15}H_{21}NO_5$
Calcd.(%): C, 61.00; H, 7.17; N, 4.74 Found (%): C, 61.14; H, 7.03; N, 4.69

EXAMPLE 8

N-(4-methylbenzyl)valienamine

In a mixture of 60 ml of methanol and 40 ml of dioxane is dissolved 3.0 g of valienamine. To the solution are added 5.1 g of sodium hydrogen carbonate and 6.0 g of p-methylbenzyl bromide, followed by stirring at room temperature for 18 hours. The reaction mixture is filtered and the filtrate is concentrated under reduced pressure. To the concentrate is added water, and the pH is adjusted to 2, followed by washing with benzene. The water layer is adjusted to pH 10 and extracted with n-butanol. The n-butanol extract is washed with water, admixed with water and subjected to concentration under reduced pressure azeotropically to give crystals of N-(4-methylbenzyl)valienamine.

Elemental analysis, for $C_{15}H_{21}NO_4$
Calcd.(%): C, 64.49; H, 7.58; N, 5.01 Found (%): C, 64.17; H, 7.71; N, 5.08

EXAMPLE 9

N-(4-bromobenzyl)valienamine

In 60 ml of methanol is dissolved 3.0 g of valienamine. To the solution are added 40 ml of dioxane, 5.0 g of sodium hydrogen carbonate and 10 g of 4-bromobenzyl bromide, followed by stirring at room temperature for 18 hours. The reaction mixture is filtered, and 100 ml of water is added to the filtrate, which is then adjusted to pH 2 and washed with benzene. The water layer is adjusted to pH 8 and extracted with ethyl acetate, whereby mainly N,N-di(4-bromobenzyl)valienamine, along with a small amount of N-(4-bromobenzyl)valienamine, moves into the ethyl acetate layer and large portion of N-(4-bromobenzyl)valienamine remains in the water layer. The water layer is extracted with n-butanol, and the n-butanol extract is subjected to concentration with water under reduced pressure azeotropically to give crystals of N-(4-bromobenzyl)valienamine. The above-mentioned ethyl acetate layer is extracted with water for extraction of N-(4-bromobenzyl)valienamine, and the water layer is concentrated under reduced pressure to give crystals of N-(4-bromobenzyl)valienamine, which are recrystallized from hot ethanol. The melting point of the recrystallized product is 190°-194° C. (decomp.)

Elemental analysis, for $C_{14}H_{18}NO_4Br$
Calcd.(%): C, 48.85; H, 5.27; N, 4.07; Br, 23.22 Found (%): C, 48.66; H, 5.28; N, 4.03; Br, 23.11

This N-(4-bromobenzyl)valienamine is confirmed as having the following structural formula by X-ray crystallographical analysis.

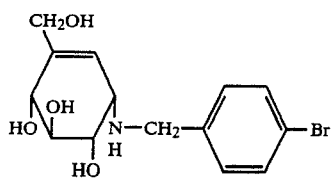

EXAMPLE 10

N-(4-carboxybenzyl)valienamine

In 20 ml of methanol is dissolved 2 g of valienamine. To the solution are added 3 g of 4-carboxybenzaldehyde, 2.8 ml of triethylamine and 5 g of magnesium sulfate followed by stirring at room temperature for 3 hours. The reaction mixture is filtered, and the filtrate is concentrated to dryness under reduced pressure. The concentrate is dissolved in 25 ml of methanol, and 700 mg of sodium borohydride is added to the solution under ice-cooling, followed by stirring at the same temperature for 1 hour. To the reaction mixture is added 300 ml of water, which is concentrated under reduced pressure to about 200 ml. The concentrated solution is adjusted to pH 2 and washed with ethyl acetate. The water layer is adjusted to pH 4.5 and then concentrated under reduced pressure to about 20 ml. The concentrated solution is chromatographed on activated carbon (250 ml) and the elution is conducted with a gradient of water (1 l)-70% methanol (1 l). The eluate (fraction No. 76-100, one fraction weighs 18 g) is concentrated under reduced pressure, and ethanol is added to the residue, thereby yielding crude crystals of N-(4-carboxybenzyl)valienamine. They are recrystallized from water-ethanol. Yield of 1.3 g.

Elemental analysis, for $C_{15}H_{19}NO_6$
Calcd.(%): C, 58.24; H, 6.19; N, 4.53 Found (%): C, 58.14; H, 6.07; N, 4.56

EXAMPLE 11

N-(3,5-di-tert-butyl-4-hydroxybenzyl)valienamine

In 30 ml of methanol is dissolved 3.0 g of valienamine. To the solution is added 7.0 g of 3,5-di-tert-butyl-4-hydroxybenzaldehyde, followed by stirring at 40° C. for 2 hours. The reaction solution is concentrated under reduced pressure, and petroleum ether is added to the residue. The resultant precipitate is collected by filtration and dried. The Schiff's base obtained is dissolved in 50 ml of methanol. To the solution is added 800 mg of sodium borohydride under ice-cooling, followed by stirring for 40 minutes. Water and acetone are added to the reaction solution, and the mixture, with n-butanol, is subjected to concentration under reduced pressure azeotropically. The residue is suspended in 100 ml of water, adjusted to pH 2 and washed with toluene. The water layer is adjusted to pH 10 and extracted with n-butanol. The n-butanol extract is washed with water and then, with water, subjected to concentration under reduced pressure azeotropically. The residue is again suspended in 100 ml of water, adjusted to pH 2 and washed with ethyl acetate. The water layer is adjusted to pH 10, and extracted with ethyl acetate. The ethyl acetate extract is concentrated under reduced pressure, and ethyl ether is added to the residue to yield 1.1 g of white powder of N-(3,5-di-tert-butyl-4-hydroxybenzyl)-valienamine.

Elemental analysis, for $C_{22}H_{35}NO_5$

Calcd.(%): C, 67.14; H, 8.97; N, 3.56 Found (%): C, 66.68; H, 9.05; N, 3.69

EXAMPLE 12

N-phenethylvalienamine

In 20 ml of methanol is dissolved 2.0 g of valienamine. To the solution is added 5 ml of a 50% solution of phenylacetaldehyde in diethyl phthalate, followed by stirring at room temperature for 4 hours. The reaction solution is concentrated under reduced pressure, and ethyl ether is added to the residue. The resultant precipitates are collected by filtration and dried under reduced pressure. The Schiff's base obtained (2.2 g) is dissolved in 25 ml of methanol, and 340 mg of sodium borohydride is added to the solution under ice-cooling, followed by stirring for 18 hours. Acetone and water are added to the reaction solution, and the organic solvent is distilled off under reduced pressure. The resultant aqueous solution is adjusted to pH 2 and washed with ethyl acetate, and the water layer is concentrated under reduced pressure. The concentrated solution is chromatographed on a column of Diaion HP-20AG (250 ml), and the elution is conducted with water. The eluate (fraction No. 23–60, one fraction weighs 18 g) is concentrated under reduced pressure and lyophilized to yield 1.3 g of N-phenethylvalienamine hydrochloride.

Elemental analysis, for $C_{15}H_{21}NO_4 \cdot HCl \cdot H_2O$

Calcd.(%): C, 53.97; H, 7.25; N, 4.20; Cl, 10.62 Found (%): C, 53.98; H, 7.45; N, 4.19; Cl, 10.67

In 20 ml of water is dissolved 1.2 g of N-phenethylvalienamine hydrochloride, and the solution is adjusted to pH 9.5 with N-sodium hydroxide. The aqueous solution is concentrated under reduced pressure to about 10 ml and allowed to stand in an ice-chamber to give crystals of N-phenethylvalienamine. Yield of 0.40 g.

Elemental analysis, for $C_{15}H_{21}NO_4$

Calcd.(%): C, 64.49; H, 7.58; N, 5.01 Found (%): C, 64.56; H, 7.58; N, 4.99

EXAMPLE 13

N-(α-methylbenzyl)valienamine

In 80 ml of dimethylformamide is dissolved 2.0 g of valienamine. To the solution are added 2 ml of triethylamine and 3 ml of α-bromoethylbenzene, followed by stirring at room temperature for 18 hours. The reaction solution is concentrated under reduced pressure, and 80 ml of water is added to the residue, which is washed with benzene. The water layer is adjusted to pH 10, washed with ethyl acetate and extracted with n-butanol. Water is added to the n-butanol extract, and the mixture is subjected to concentration under reduced pressure azeotropically. The resultant aqueous solution is chromatographed on a column of Diaion HP-20AG (60 ml), and the elution is conducted with water. The eluate (fraction No. 3–11, one fraction weighs 18 g) is concentrated to dryness under reduced pressure, and ethanol is added to the residue to yield white powder of N-(α-methylbenzyl)valienamine. Yield of 0.4 g.

Elemental analysis, for $C_{15}H_{21}NO_4 \cdot H_2O$

Calcd.(%): C, 60.59; H, 7.80; N, 4.71 Found (%): C, 60.18; H, 7.60; N, 4.74

EXAMPLE 14

N-(2-diphenylethyl)valienamine

In 30 ml of methanol is dissolved 2.0 g of valienamine. To the solution is added 4.0 g of diphenylacetaldehyde followed by stirring at room temperature for 2 hours. The reaction solution is concentrated under reduced pressure to distill off the methanol, and ethyl ether is added to the residue. The resultant precipitate is recovered by filtration and dried. The Schiff's base obtained is dissolved in 40 ml of methanol. To the solution is added 400 mg of sodium borohydride under ice-cooling, followed by stirring at room temperature for 40 minutes. Water and acetone are added to the reaction solution, which, with n-butanol, is subjected to concentration under reduced pressure azeotropically. 100 ml of water is added to the residue, and the mixture is adjusted to pH 2 and washed with toluene and ethyl acetate. The water layer is adjusted to pH 10 and extracted with n-butanol. The n-butanol extract is washed with water, and then subjected to concentration with water, under reduced pressure azeotropically. Ethyl ether is added to the residue to precipitate N-(2-diphenylethyl)-valienamine. Yield of 0.4 g.

Elemental analysis, for $C_{21}H_{25}NO_4$

Calcd.(%): C, 70.96; H, 7.09; N, 3.94 Found (%): C, 70.51; H, 7.09; N, 4.07

EXAMPLE 15

N-(β-hydroxyphenethyl)valienamine

In 20 ml of methanol are dissolved 2.0 g of valienamine and 3.0 g of phenylglyoxal monohydrate. To the solution is added 5.0 g of magnesium sulfate, followed by stirring at room temperature for 18 hours. The reaction mixture is filtered, and the filtrate is concentrated to dryness under reduced pressure. Ethyl ether is added to the concentrate, and the resultant precipitate is collected by filtration. 3.1 g of the Schiff's base thus obtained is dissolved in 25 ml of methanol, and 1.25 g of sodium borohydride is added to the solution under ice-cooling, followed by stirring for 3 hours. Acetone and water are added to the reaction solution, which is subjected to concentration with n-butanol under reduced pressure azeotropically. The resultant water layer is adjusted to pH 2 and washed with ethyl acetate. The water layer is adjusted to pH 9 and concentrated under reduced pressure, and the residue is chromatographed on a column (250 ml) of Diaion HP-20AG. The elution is conducted with a gradient of water-80% aqueous methanol and the eluate is concentrated under reduced pressure and lyophilized to give 1.2 g of white powder of N-(β-hydroxyphenethyl)-valienamine.

Elemental analysis, for $C_{15}H_{21}NO_5 \cdot \frac{1}{2}H_2O$

Calcd.(%): C, 59.19; H, 7.29; N, 4.60 Found (%): C, 59.46; H, 7.38; N, 4.57

EXAMPLE 16

N-(2-methoxy-β-hydroxyphenethyl)valienamine

To a solution of 3.0 g of valienamine in 10 ml of dimethylsulfoxide is added a solution of 2.85 g of 2- methoxyphenylglyoxal.monohydrate in 3.5 ml of dimethylsulfoxide, and the mixture is stirred at room temperature for 1 hour. 70 ml of ethanol is added to the reaction solution, which is stirred at room temperature for 30 minutes. 900 mg of sodium borohydride is added to the solution, followed by stirring at room temperature for 2.5 hours. The reaction solution is concentrated under reduced pressure to remove the solvent, and 300 ml of water is added to the concentrate, which is adjusted to pH 2 and admixed with 50 ml of ethyl acetate. The mixture is stirred, and then is subjected to separation to remove the ethyl acetate layer. Further, the water layer is washed with ethyl acetate, adjusted to pH 10 and extracted with n-butyl alcohol. The n-butyl alcohol extract is washed with water and subjected to concentration with water under reduced pressure azeotropically. Ethyl ether is added to the concentrate, and the resultant precipitates are collected by filtration. The precipitates are suspended in 50 ml of water, which is adjusted to pH 2 to make a solution. The solution is chromatographed on a column (250 ml) of Diaion HP-20AG, and the elution is conducted with water. The eluate (frac. No. 35-70, one fraction weighs 18 g) is concentrated under reduced pressure to about 50 ml, which is adjusted to pH 10 and extracted with n-butyl alcohol. The extract is washed with water, and concentrated to dryness under reduced pressure. The residue is dissolved in ethanol, and ethyl ether is added to the solution to yield crystals of N-(2-methoxy-$\beta$-hydroxyphenethyl)-valienamine. Yield of 0.6 g.

Elemental analysis, for $C_{16}H_{23}NO_6$

Calcd.(%): C, 59.06; H, 7.13; N, 4.31 Found (%): C, 58.76; H, 7.04; N, 4.31

EXAMPLE 17

N-(2-chloro-$\beta$-hydroxyphenethyl)valienamine

In 12 ml of dimethylsulfoxide are dissolved 3 g of valienamine and 3 g of 2-chlorophenylglyoxal.monohydrate, and the solution is stirred at room temperature for 1 hour. 66 ml of methanol is added to the reaction solution, and the mixture is stirred at room temperature for 30 minutes, followed by adding 900 mg of sodium borohydride in two portions. The reaction solution is further stirred at room temperature for 2.5 hours and the solution is, after the addition of water, acetone and n-butanol, concentrated under reduced pressure. The residue is suspended in 200 ml of water, adjusted to pH 2 and washed with ethyl acetate. The water layer is concentrated under reduced pressure, and the residue is chromatographed on a column (250 ml) of Diaion HP-20AG, and the elution is conducted with water. The eluate (fraction No. 42-115, one fraction weighs 18 g) is concentrated under reduced pressure, and the concentrated solution is adjusted to pH 10 and extracted with three portions of n-butanol. The n-butanol extracts are combined and concentrated under reduced pressure, and the concentrate is dissolved in a small amount of ethanol. Ethyl ether is added to the ethanol solution, and there separated out the precipitate of (2-chloro-$\beta$-hydroxyphenethyl)valienamine. Yield of 0.9 g.

Elemental analysis, for $C_{15}H_{20}NO_5Cl.\frac{1}{2}H_2O$

Calcd.(%): C, 53.18; H, 6.25; N, 4.13; Cl, 10.46 Found (%): C, 53.51; H, 6.64; N, 3.96; Cl, 10.22

EXAMPLE 18

N-(1,3-dihydroxy-2-propyl)valienamine

In 50 ml of dimethylsulfoxide is dissolved 2.0 g of valienamine. To the solution are added 3.4 g of dihydroxyacetone, 1.5 ml of 2N hydrochloric acid and 2.6 g of sodium cyanoborohydride. The mixture is stirred at 60° to 65° C. for 18 hours, followed by removing dimethylsulfoxide as far as possible by distillation under reduced pressure. The residue is dissolved in water, and the solution is passed through a column (200 ml) of Dowex 1×2 (OH$^-$ type) (manufactured by Dow Chemical Co. U.S.A.) and a column (180 ml) of Amberlite CG-50 (NH$_4^+$ type). The effluent is adsorbed on a column (100 ml) of Amberlite CG-50 (N$^+$ type), and the column is washed with water (500 ml), followed by conducting the elution with 0.5N aqueous ammonia (500 ml). The eluate is concentrated to dryness under reduced pressure, and the resultant syrupy substance is again chromatographed on a column (100 ml) of Dowex 1×2 (OH$^-$ type). The column is subjected to elution with water. The eluate (fraction No. 17-23, one fraction weighs 15 g) is concentrated to dryness under reduced pressure, and the concentrate is recrystallized from hot acetone.

Elemental analysis, for $C_{10}H_{19}NO_6$

Calcd.(%): C, 48.18; H, 7.68; N, 5.62 Found (%): C, 48.21; H, 7.71; N, 5.43

EXAMPLE 19

N-(3-phenylpropyl)valienamine

In 20 ml of methanol is dissolved 2.0 g of valienamine. To the solution is added 2.7 g of $\beta$-phenylpropionaldehyde. The mixture is stirred at room temperature for 2 hours. The reaction solution is concentrated under reduced pressure, and ethyl ether is added to the residue. The resultant precipitate is collected by filtration and dried. 2.3 g of the Schiff's base thus obtained is dissolved in 20 ml of methanol. To the solution is added 340 mg of sodium borohydride under ice-cooling, followed by stirring for 1 hour. Water and acetone are added to the reaction solution, which is then concentrated under reduced pressure to distill off the organic solvents. The resultant aqueous solution is adjusted to pH 2 and washed with ethyl acetate. The water layer is concentrated to about 30 ml, which is then chromatographed on a column (250 ml) of Diaion HP-20AG, followed by elution with water. The eluate (fraction No. 34-110, one fraction weighs 18 g) is concentrated under reduced pressure to about 50 ml, which is adjusted to pH 9.5 and allowed to stand to yield crystals of N-(3-phenylpropyl)valienamine. Yield of 0.8 g.

Elemental analysis, for $C_{16}H_{23}NO_4$

Calcd.(%): C, 65.51; H, 7.90; N, 4.78 Found (%): C, 65.23; H, 8.09; N, 4.84

EXAMPLE 20

N-(3-phenylallyl)valienamine

In 20 ml of methanol is dissolved 2 g of valienamine. To the solution is added 2.6 ml of cinnamaldehyde, followed by stirring at room temperature for 2 hours. The reaction solution is concentrated under reduced pressure, and ethyl ether is added to the concentrate. The resultant precipitate is collected by filtration and dried. 2.5 g of the Schiff's base thus obtained is dissolved in 30 ml of methanol, and 350 mg of sodium borohydride is added to the solution under ice-cooling, followed by stirring at the same temperature for 1 hour. Water, acetone and n-butanol are added to the reaction solution, which is then concentrated under reduced pressure to distill off the organic solvents. The resultant aqueous solution is adjusted to pH 2, washed with ethyl acetate and concentrated to about 30 ml under reduced pressure. The concentrated solution is chromatographed on a column (250 ml) of Diaion HP-20AG, and the elution is conducted with water. The eluate (fraction No. 28-120, one fraction weighs 18 g) is concentrated under reduced pressure, and the concentrated solution is adjusted to pH 9.5 to give crystals of N-(3-phenylallyl)valienamine. Yield of 1.53 g Elemental analysis, for $C_{16}H_{21}NO_4$ Calcd.(%): C, 65.95; H, 7.27; N, 4.81 Found (%): C, 65.85; H, 7.41; N, 4.76

EXAMPLE 21

N-($\alpha$-methylphenethyl)valienamine

In 80 ml of dimethylformamide is dissolved 3 g of valienamine. To the solution are added 5.04 g of sodium hydrogen carbonate and 8 ml of 2-bromo-1-phenylpropane, followed by stirring for 2 days under heating at 60° to 65° C. The reaction solution is concentrated under reduced pressure, and the residue is suspended in 100 ml of water, adjusted to pH 2 and washed with ethyl acetate. The water layer is adjusted to pH 10 and extracted with three portions each of 50 ml of n-butanol. The n-butanol extracts are combined, washed with water and concentrated under reduced pressure. The concentrate is chromatographed on a column (100 ml) of Diaion HP-20AG, and the elution is carried out with a water-methanol gradient. The eluate is concentrated to dryness under reduced pressure, and the concentrate is dissolved in ethanol and again concentrated to dryness under reduced pressure. The residue is dried overnight in a desiccator to yield white powder of N-($\alpha$-methylphenethyl)-valienamine. $IC_{50}$($\alpha$-glucosidase, yeast): $0.13 \times 10^{-6}M$.

EXAMPLE 22

N-($\beta$-methylphenethyl)valienamine

In 20 ml of methanol is dissolved 2.0 g of valienamine. To the solution is added 2.6 g of $\alpha$-phenylpropionaldehyde, followed by stirring at room temperature for 2 hours. Ethyl ether and petroleum ether are added to the reaction solution, and the resultant precipitate is collected by filtration and dried. The Schiff's base thus obtained is dissolved in 40 ml of methanol. To the solution is added 400 ml of sodium borohydride under ice-cooling, followed by stirring for 40 minutes. Water and acetone are added to the reaction solution, which is then concentrated under reduced pressure to distill off the organic solvents. The concentrated solution is adjusted to pH 2 and washed with benzene. The water layer is adjusted to pH 10 and extracted with n-butanol. The n-butanol extract, after the addition of water, is concentrated under reduced pressure, and the concentrate is chromatographed on a column (100 ml) of Diaion HP-20AG, followed by conducting the elution with a water (1 l)-80% aqueous methanol (1 l) gradient. The eluate (fraction No. 56-76, one fraction weighs 18 g) is concentrated to dryness under reduced pressure, and the residue is recrystallized from hot ethyl acetate.

Elemental analysis, for $C_{16}H_{23}NO_4$

Calcd.(%): C, 65.51; H, 7.90; N, 4.78 Found (%): C, 65.97; H, 8.37; N, 4.78

EXAMPLE 23

N-(3-phenoxypropyl)valienamine

In 60 ml of methanol is dissolved 3.0 g of valienamine. To the solution are added 40 ml of dioxane, 5.0 g of sodium hydrogen carbonate and 8.6 g of 3-bromo-1-phenoxypropane, followed by stirring at 70° C. for 2 days. The reaction mixture is filtered, and the filtrate is concentrated to dryness under reduced pressure. 100 ml of water is added to the concentrate, and the mixture is adjusted to pH 2 and washed with benzene. The water layer is adjusted to pH 8, washed with ethyl acetate, adjusted to pH 10, and extracted with n-butanol. The n-butanol extract, with water, is subjected to concentration under reduced pressure azeotropically to give crystals of N-(3-phenoxypropyl)-valienamine. Yield of 1.7 g.

Elemental analysis, for $C_{16}H_{23}NO_5$

Calcd.(%): C, 62.12; H, 7.49; N, 4.53 Found (%): C, 62.15; H, 7.56; N, 4.64

EXAMPLE 24

N-n-butylvalienamine

In 50 ml of methanol-dioxane (3:2) are dissolved 2 g of valienamine and 2.8 g of 1-bromobutane. To the solution is added 5 g of sodium hydrogen carbonate, followed by stirring at 70° C. for 50 hours. The reaction mixture is filtered, and insoluble matter is washed with methanol. The filtrate and washings are combined and concentrated under reduced pressure. The concentrate is dissolved in a small amount of water, and the solution is adjusted to pH 2 and chromatographed on a column (250 ml) of activated carbon, followed by elution with water. The eluate (fraction No. 51-100, one fraction weighs 18 g) is concentrated under reduced pressure, and the concentrate is chromatographed on a column (200 ml) of Dowex 1×2 ($OH^-$ type), followed by conducting the elution with water. The eluate (fraction No. 11-25, one fraction weighs 18 g) is concentrated under reduced pressure and lyophilized to yield N-n-butyl-valienamine.

Elemental analysis, for $C_{11}H_{21}NO_4$

Calcd. (%): C, 57.12; H, 9.15; N, 6.06 Found (%): C, 56.94; H, 9.58; N, 5.93

EXAMPLE 25

N-(4-phenylbutyl)valienamine

In 60 ml of methanol is dissolved 3.0 g of valienamine. To the solution are added 40 ml of dioxane, 2.6 g of sodium hydrogen carbonate and 9.0 g of 4-bromo-1-phenylbutane, followed by stirring at 70° C. for 18 hours. The reaction mixture is filtered, and the filtrate is concentrated to dryness under reduced pressure. To the concentrate is added 150 ml of water, which is then adjusted to pH 2 and washed with toluene. The water layer is adjusted to pH 10, washed with ethyl acetate, and extracted with n-butanol. The n-butanol extract is subjected to concentration with water under reduced pressure azeotropically, and the residue is crystallized from ethanol-ethyl ether. Yield of 1.2 g.

Elemental analysis, for $C_{17}H_{25}NO_4$

Calcd. (%): C, 66.42; H, 8.20; N, 4.56 Found (%): C, 66.17; H, 8.38; N, 4.50

EXAMPLE 26

N-(5-phenylpentyl)valienamine

In a mixture of 60 ml of methanol and 40 ml of dioxane is dissolved 3.0 g of valienamine. To the solution are added 2.6 g of sodium hydrogen carbonate and 10 g of 1-bromo-5-phenylpentane, followed by stirring at 70° C. for 18 hours. The reaction solution is concentrated under reduced pressure, and 100 ml of water is added to the residue, which is then adjusted to pH 4 and extracted with n-butanol. The n-butanol extract is subjected to concentration with water under reduced pressure, azeotropically, and the residue is crystallized from ethanol-ethyl ether, and recrystallized from water.

Elemental analysis, for $C_{18}H_{27}NO_4$

Calcd. (%): C, 67.26; H, 8.47; N, 4.36 Found (%): C, 67.22; H, 8.51; N, 4.55

EXAMPLE 27

N-(6-phenylhexyl)valienamine

In 50 ml of ethyl acetate are dissolved 1.8 g of 6-phenylhexanoic acid and 1.3 g of N-hydroxysuccinimide. To the solution is added 2.2 g of dicyclohexylcarbodiimide under ice-cooling, followed by stirring at the same temperature for 1 hour and further at room temperature for 1 hour. The separated insoluble matter is filtered out and the filtrate is concentrated to dryness under reduced pressure. The residue is dissolved in 20 ml of dimethylformamide. To the solution is added 1.9 g of valienamine, followed by stirring at room temperature for 2 hours. The reaction solution is concentrated under reduced pressure, and the residue is dissolved in n-butanol. The n-butanol solution is washed with water and concentrated under reduced pressure, and the concentrate is chromatographed on a column of 250 ml of Amberlite CG-50 (H+ type). The column is washed with water, (1 l) and the elution is conducted with methanol (500 ml). The eluate is concentrated under reduced pressure, and the residue is dissolved in n-butanol, which is then washed with water and concentrated under reduced pressure. Ethyl ether is added to the concentrate to give precipitate of N-(6-phenylhexanoyl)valienamine. Yield of 2.2 g.

In 100 ml of tetrahydrofuran is dissolved 2.0 g of N-(6-phenylhexanoyl)valienamine. To the solution is added 2 g of lithium aluminium hydride under ice-cooling, followed by stirring at room temperature for 6 hours. The reaction solution is poured into 200 ml of ice water, and 2N HCl is added dropwise to the mixture to adjust to pH 3, followed by filtration. The filtrate is concentrated to about 50 ml, and the concentrated solution is chromatographed on a column (250 ml) of Diaion HP-20AG. The column is washed with water (1 l) and 50% aqueous methanol (1 l), followed by elution with methanol (50 ml). The eluate is concentrated under reduced pressure, and the concentrate is dissolved in water. The solution is adjusted to pH 11.5 and extracted with ethyl acetate. The ethyl acetate extract is washed with water, dried over sodium sulfate and concentrated under reduced pressure. Ethyl ether is added to the concentrate to give precipitate of N-(6-phenylhexyl)valienamine.

EXAMPLE 28

N-(L-xylo-2,3,4,5-tetrahydroxy-1-hydroxymethylphentyl)valienamine

In 50 ml of dimethylsulfoxide are dissolved 2.0 g of valienamine, 6.5 g of L-sorbose and 2.5 g of sodium cyanoborohydride. To the solution is added 1.5 ml of 2N-hydrochloric acid, followed by stirring at 60° to 65° C. for 36 hours. The reaction solution is concentrated under reduced pressure, and the concentrate is dissolved in water and purified successively by column chromatography on Dowex 1×2 (OH− type) (eluted with water: frac. No. 12–26,*), column chromatography on Amberlite CG-50 (NH$_4$+ type) (eluted with water: frac. No. 4–6,*) and column chromatography on Amberlite CG-50 (H+ type) (eluted with 0.5N aqueous ammonia: frac. No. 49–53,*) in this order, followed by purification by column chromatography (300 ml) on Dowex 1×2 (OH− type) (eluted with water). The eluate (frac. No. 21–50,*) is concentrated under reduced pressure, and to the resultant syrupy substance is added ethyl ether to give white poweder.

*one fraction weighs 18 g.

Elemental analysis, for $C_{13}H_{25}NO_9 \cdot \frac{1}{2}H_2O$

Calcd. (%): C, 44.82; H, 7.52; N, 4.02 (Found (%): C, 44.90; H, 8.01; N, 3.98

EXAMPLE 29

N-(D-gluco-2,3,4,5,6-pentahydroxyhexyl)valienamine

In 20 ml of dimethylformamide are suspended 1.77 g of valienamine and 2.7 g of D-glucose, and the suspension is stirred at 37° C. for 48 hours. To the reaction mixture is added 200 ml of acetone, and the resultant precipitate is collected by filtration. The precipitate is dissolved in 100 ml of water, and 750 mg of sodium borohydride is added little by little to the solution with stirring. The reaction mixture is allowed to stand at room temperature for 18 hours and acidified with acetic acid, and adsorbed on a column of Dowex 50W×8 (H+ type, 100 ml). The column is washed with water (500 ml), and eluted with 0.5N aqueous ammonia (2 l). The eluate is concentrated to dryness under reduced pressure, and the concentrate is crystallized from 90% aqueous ethanol. Yield of 1.8 g.

Elemental analysis, for $C_{13}H_{25}NO_9$

Calcd. (%): C, 46.01; H, 7.43; N, 4.13 Found (%): C, 46.08; H, 7.60; N, 3.86

EXAMPLE 30

N-geranylvalienamine

In 80 ml of dimethylformamide is dissolved 3 g of valienamine. To the solution are added 5.0 g of sodium hydrogen carbonate and 8 ml of geranyl chloride, followed by stirring at room temperature for 18 hours. The reaction mixture is filtered, and the filtrate is concentrated under reduced pressure. 100 ml of water is added to the residue, which is then adjusted to pH 2 and washed with toluene. The water layer is adjusted to pH 10 and extracted with n-butanol. The n-butanol extract is concentrated under reduced pressure, and the residue is crystallized from ethanol-ethyl ether. Yield of 1 g.

Elemental analysis, for $C_{17}H_{29}NO_4$

Calcd. (%): C, 65.56; H, 9.39; N, 4.50 Found (%): C, 65.41; H, 9.30; N,, 4.40

EXAMPLE 31

By employing the same procedure as the synthetic method for N-(D-gluco-2,3,4,5,6-pentahydroxyhexyl)-valienamine (referred to briefly as "Gluco-H") described in Example 29, there are synthesized the following valienamine derivatives from the corresponding staritng compounds:

N-(D-manno-2,3,4,5,6-pentahydroxyhexyl)valienamine (referred to briefly as "Manno-H") through the reaction of valienamine with D-mannose;

N-(D-galacto-2,3,4,5,6-pentahydroxyhexyl)valienamine (referred to briefly as "Galacto-H") through the reaction of valienamine with D-galactose;

N-(D-arabo-2,3,4,5-tetrahydroxypentyl)valienamine (referred to briefly as "Arabino-H") through the reaction of valienamine with D-arabinose;

N-(D-ribo-2,3,4,5-tetrahydroxypentyl)valienamine (referred to briefly as "Ribo-H") through the reaction of valienamine with D-ribose;

N-(D-xylo-2,3,4,5-tetrahydroxypentyl)valienamine (referred to briefly as "Xylo-H") through the reaction of valienamine with D-xylose; and, N-(D-arabo-2,3,4,5-tetrahydroxy-1-hydroxymethylpentyl)valienamine (referred to briefly as "Fructo-H") through the reaction of valienamine with D-fructose;

Indicated in the following are the Rf values (tlc) of these compounds by thin-layer chromatography (silica gel G: Solvent system; n-propanol.acetic acid.water=4:1:1) and the retention times of the trimethylsilyl derivatives of these compounds in gas chromatography [1.5% OV-17, Shimalite W (manufactured by Shimadzu Seisakusho, Ltd. Japan), glass column (0.3×200 cm), column temperature of 250° C.].

EXAMPLE 32

N-(2-hydroxy-3-phenoxypropyl)valienamine

In an aqueous solution (10 ml) of sodium hydroxide (2.2 g) is dissolved 4.7 g of phenol under nitrogen atmosphere. To the solution is added 5 g of epichlorohydrin, followed by stirring at room temperature for 24 hours. The reaction mixture supplemented with 50 ml of water is subjected to extraction twice with 50 ml each portion of dichloromethane.

The combined dichloromethane extracts are washed with water, dried over sodium sulfate, and concentrated under reduced pressure to give a mixture of 1-phenoxy-2,3-epoxypropane and 1-chloro-2-hydroxy-3-phenoxypropane.

In 80 ml of N,N-dimethylformamide is dissolved 2.0 g of valienamine and to the solution are added 5.8 g of sodium hydrogen carbonate and about 7 g of the above mentioned mixture, that is 1-phenoxy-2,3-epoxypropane and 1-chloro-2-hydroxy-3-phenoxypropane, followed by stirring overnight on a bath heated at 90° C.

The reaction mixture is filtered and the filtrate is concentrated under reduced pressure. To the residue are added water and n-butylalcohol and the mixture is adjusted to pH 2 with 2N hydrochloric acid, followed by separation of the water layer. The remaining n-butylalcohol layer is extracted with water. The water layers are combined and concentrated under reduced pressure. The residue is chromatographed on a column (250 ml) of MCI Gel CHP 20P (manufactured by Mitsubishi Chemical Industries, Ltd., Japan) by the use of water as the eluent.

The eluate (fraction No. 31-80, one fraction weighs 18 g) is concentrated under reduced pressure and then lyophilized to give 1.25 g of N-(2-hydroxy-3-phenoxypropyl)valienamine hydrochloride as white powder.

Elemental analysis, for $C_{16}H_{23}NO_6.HCl.\frac{1}{2}H_2O$

Calcd. (%): C, 51.82; H, 6.80; N, 3.78; Cl, 9.56 Found (%): C, 51.93; H, 7.01; N, 3.97; Cl, 10.05

$[\alpha]_D^{23}+54.4°$ (c=1, $H_2O$)

In 20 ml of water is dissolved 600 mg of N-(2-hydroxy-3-phenoxypropyl)valienamine hydrochloride. The solution is adjusted to pH 10.4 with 1N sodium hydroxide, and chromatographed on a column of MCI Gel CHP-20P (150 ml, manufactured by Mitsubishi Chemical Industries, Ltd., Japan). The column is washed with water (600 ml), followed by conducting the elution with a gradient of water (1 l)—80% aq. methanol (1 l). The eluate (fraction No. 75-88, one fraction weighs 18 g) is concentrated to about 20 ml under reduced pressure. The residue is allowed to stand overnight in a refrigerator to give 108 mg of N-(2-hydroxy-3-phenoxypropyl)valienamine as crystals.

Elemental analysis, for $C_{16}H_{23}NO_6$

Calcd. (%): C, 59.06; H, 7.13; N, 4.31 Found (%): C, 59.00; H, 7.08; N, 4.13

$[\alpha]_D^{27}+104.9°$ (c=1, $H_2O$)

EXAMPLE 33

N-(β-hydroxyphenethyl)valienamine and N-[α-(hydroxymethyl)-benzyl]valienamine In 300 ml of methanol are dissolved 10 g of valienamine and 12 ml of styrene oxide, and the solution is refluxed for 4 hours. To the reaction mixture is added 10 ml of styrene oxide and the mixture is further refluxed for 4 hours.

The reaction mixture is concentrated under reduced pressure. To the residue are added water and ethylacetate. The mixture is then shaken, which is left standing to form two layers. The water layer is separated and concentrated under reduced pressure. The residue is chromatographed on a column of Dowex 1×2 (OH⁻ type, 550 ml, manufactured by Dow Chemical Co. U.S.A.) by the use of water as the eluent. The eluate (frac. No. 71-312,*) is concentrated under reduced pressure and the residue is chromatographed on a column of amberlite CG 50 ($NH_4^+$ type, 1 l, Rohm & Haas Co. U.S.A.) by the use of water as the eluent. N-[α-(hydroxymethyl)benzyl]valienamine is first eluted, and then N-(β-hydroxyphenethyl)valienamine is eluted. Each eluate (the former: frac. No. 42-55, the latter: frac. No. 73-220*) is concentrated under reduced pressure and then lyophilized to give 2.9 g of N-[α-(hydroxymethyl)benzyl]valienamine and 6 g of N-(β-hydroxyphenethyl)valienamine as white powder respectively. N-(β-hydroxyphenethyl)valienamine.

*one fraction weighs 18 g

Elemental analysis, for $C_{15}H_{21}NO_5.\frac{1}{2}H_2O$

Calcd. (%): C, 59.19; H, 7.29; N, 4.60 Found (%): C, 59.14; H, 7.43; N, 4.69

$[\alpha]_D^{27}+108.6°$ (c=1, $H_2O$) NMR($D_2O$) δ: 2.7-3.3 (2H,—NH—C$\underline{H}_2$—), 4.7-5.1

(1H,$C_6H_5$—C$\underline{H}$—OH), 5.9-6.1(1H,6-CH), 7.59(5H,s,$C_6\underline{H}_5$—) N-[α-(hydroxymethyl)benzyl]valienamine Elemental analysis, for $C_{15}H_{21}NO_5.\frac{1}{2}H_2O$ Calcd. (%): C, 59.19; H, 7.29; N, 4.60 Found (%): C, 59.61; H, 7.30; N, 4.67

$[\alpha]_D^{27} + 120.6°$ (c=1, H$_2$O)

EXAMPLE 34

N-(1,3-dihydroxy-1-phenyl-2-propyl)valienamine

In 15 ml of methanol is dissolved 1 g of valienamine. To the solution, after addition of 10 ml of dioxane, are added 2.3 g of 2-bromo-1,3-dihydroxy 1-phenylpropane and 1.2 g of sodium hydrogen carbonate followed by stirring at 70° C. for 3 days. The reaction mixture is filtered and insolubles are washed with methanol. The filtrate and the washing are combined and the combined solution is concentrated under reduced pressure. Water is added to the residue and adjusted to pH 2 with 2N hydrochloric acid, followed by washing with ethyl acetate. The water layer is concentrated under reduced pressure and the residue is chromatographed on a column of MCI Gel CHP 20P (350 ml, Mitsubishi Chemical Industries Ltd., Japan), by the use of water as the eluent.

The eluate (fraction No. 29-46, one fraction weighs 18 g) is concentrated under reduced pressure, and lyophilized to give 1.1 g of N-(1,3-dihydroxy-1-phenyl-2-propyl)valienamine hydrochloride as white powder.

Elemental analysis, for C$_{16}$H$_{23}$NO$_6$·HCl·1½H$_2$O

Calcd. (%): C, 49.42; H, 7.00; N, 3.60; Cl, 9.12 Found (%): C, 49.33; H, 6.76; N, 3.99; Cl, 9.58

$[\alpha]_D^{23} + 34.4°$ (c=1, H$_2$O)

EXAMPLE 35

N-(3,4-dihydroxybenzyl)valienamine

In 30 ml of methanol are dissolved 2 g of valienamine and 8.0 g of 3,4-di-(tetrahydropyranyloxy)benzaldehyde, and the resultant mixture is stirred at room temperature for 2 hours. The reaction mixture is concentrated under reduced pressure and ethyl ether is added to the concentrate. The resulting precipitates are collected by filtration and dried to give a Schiff's base. The base is dissolved in 50 ml of methanol, to which is added 700 mg of sodium borohydride little by little to the solution under ice-cooling, followed by stirring under ice-cooling for 2 hours. To the reaction mixture are added water, acetone and n-butyl alcohol. The mixture is concentrated under reduced pressure to distill off the organic solvents. The remaining aqueous solution is chromatographed on a column of MCI Gel CHP 20P (250 ml, Mitsubishi Chemical Industries. Ltd., Japan) by the use of water (800 ml) for washing the column. The elution is conducted with a gradient of water(1 l)-methanol (1 l). The eluate (fraction 61-78, one of fraction weighs 18 g) is concentrated to dryness under reduced pressure to give 3.3 g of N-[3,4-di-(tetrahydropyranyloxy)benzyl]valienamine.

In 110 ml of 0.5N sulfuric acid is dissolved 2.2 g of N-[3,4-di(tetrahydropyranyloxy)benzyl]valienamine, followed by stirring at room temperature overnight.

The resultant mixture is, after adjusted to pH 5 with barium hydroxide, subjected to filtration, and the filtrate is concentrated under reduced pressure. The concentrate is adjusted to pH 7.5 and chromatographed on a column of MCI Gel CHP 20P (400 ml, Mitsubishi Chemical & Industries, Ltd. Japan) by the use of water (1 l) for elution The eluate (fraction No. 21-30, one fraction weighs 18 g) is concentrated under reduced pressure, and then lyophilized to give 880 mg of N-(3,4-dihydroxybenzyl)-valienamine.

Elemental analysis, for C$_{14}$H$_{19}$NO$_6$

Calcd. (%): C, 56.56; H, 6.44; N, 4.71 Found (%): C, 56.38; H, 6.51; N, 4.32

$[\alpha]_D^{23} + 76.7°$ (c=1, H$_2$O)

EXAMPLE 36

N-(2-hydroxycyclohexyl)valienamine

In 100 ml of methanol is dissolved 2.0 g of valienamine. To the solution is added 6 ml of 1,2-epoxycyclohexane, followed by refluxing with stirring for 9 hours.

The reaction mixture is concentrated under reduced pressure. To the residue is added ethyl ether to give precipitates. The precipitates collected by filtration are dissolved in a small volume of water, and the solution is chromatographed on a column (400 ml) of Amberlite CG-50 (NH$_4^+$ type, Rhom & Hass U.S.A.) by the use of water (1.5 l) for elution. The eluate (the latter half) is concentrated under reduced pressure and the resultant is lyophilized to give 1.1 g of N-(2-hydroxycyclohexyl)-valienamine.

$[\alpha]_D^{24} + 61.1°$ (c=1, H$_2$O)

Elemental analysis for C$_{13}$H$_{23}$NO$_5$·½H$_2$O

Calcd. (%): C, 55.30; H, 8.75; N, 4.96 Found (%): C, 55.78; H, 8.73; N, 4.93

IC$_{50}$ (saccharase): $1.7 \times 10^{-7}$M

The inhibitory activity against saccharase prepared from porcine intestinal mucosa is determined by a similar method to that against maltase in accordance with the method described in Acta. Chem. Scand., 12, 1997-2006 (1958).

EXAMPLE 37

N-(2-hydroxycyclopentyl)valienamine

To 2.0 g of valienamine dissolved in 100 ml of methanol is added 6 ml of 1,2-epoxycyclopentane. The mixture is refluxed for 24 hours and concentrated under reduced pressure. To the residue is added ethyl ether to give precipitates, which are collected by filtration.

The precipitates are dissolved in small volume of water, and the solution is chromatographed on a column (400 ml) of Amberlite CG50 (NH$_4^+$, Rohm & Haas U.S.A.), by the use of water (1 l) for elution.

The eluate (the latter half) is concentrated under reduced pressure and lyophilized to give 0.8 g of N-(2-hydroxycyclopentyl)-valienamine as white poweder.

Elemental analysis, for C$_{12}$H$_{21}$NO$_5$·¼H$_2$O

Calcd. (%): C, 54.63; H, 8.22; N, 5.31 Found (%): C, 54.59; H, 8.07; N, 5.31

$[\alpha]_D^{24} + 112.2°$ (c=1, H$_2$O)

EXAMPLE 38

To 200 ml of a beverage admixed with fruit juice is added 50 mg of N-(1,3-dihydroxy-2-propyl)valienamine, followed by stirring for dissolution. The mixture is stirred and uniformly mixed to produce a beverage admixed with fruit juice.

EXAMPLE 39

After the completion of the production steps for apricot jam (cooking and heating treatment) in accordance with the conventional method, and when the temperature of the resultant jam decreased to about 55° C., N-(2-methoxy-β-hydroxyphenyl)valienamine hydrochloride is uniformly blended into it at a rate of 0.5% relative to the finished product weight, followed by cooling to obtain the apricot jam product.

EXAMPLE 40

N-(β-hydroxyphenethyl)valienamine hydrochloride:

20 parts by weight

Lactose:

100 parts by weight

The above two are uniformly mixed and processed into a form of powder or fine granule to produce a powder preparation.

I claim:

1. A compound of formula

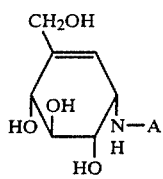

wherein A is a member of the class consisting of —CH₂CH₂—phenyl, —CH₂CH₂CH₂—phenyl, —CH₂—CH(OH)—phenyl, —CH(CH₂OH)—CH(OH)—phenyl, —CH(CH₂OH)₂, and 3,4-dihydroxybenzyl.

2. A compound as claimed in claim 1 wherein A is a chain hydrocarbon of 1 to 6 carbon atoms optionally substituted by hydroxyl or a phenyl group optionally substituted by hydroxyl, lower alkoxy, lower alkyl or halogen.

3. A compound as claimed in claim 1 or 2, which is N-(1,3-dihydroxy-2-propyl)valienamine.

4. A compound is claimed in claim 1 or 2, which is N-(β-hydroxyphenethyl)valienamine.

5. An α-glucosidase inhibitor which contains an effective inhibitory amount of a compound of formula

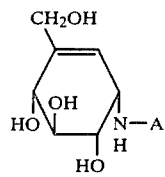

wherein A is a member of the class consisting of —CH₂CH₂—phenyl, —CH₂CH₂CH₂—phenyl, —CH₂—CH(OH)—phenyl, —CH(CH₂OH)—CH(OH)—phenyl, —CH(CH₂OH)₂, and 3,4-dihydroxybenzyl.

* * * * *